United States Patent [19]

Codignola

[11] 4,438,285

[45] Mar. 20, 1984

[54] PROCESS FOR THE CATALYTIC HYDROGENATION OF 1-4-BUTYNEDIOL TO 1-4 BUTANEDIOL

[75] Inventor: Franco Codignola, Buenos Aires, Argentina

[73] Assignee: S.I.S.A.S. Societa Italina Serie Acetica Sintetica S.p.A., Milan, Italy

[21] Appl. No.: 320,913

[22] Filed: Nov. 12, 1981

Related U.S. Application Data

[60] Continuation of Ser. No. 184,838, Sep. 8, 1980, abandoned, which is a division of Ser. No. 49,245, Jun. 18, 1979, abandoned.

[30] Foreign Application Priority Data

Jun. 16, 1978 [IT] Italy ............................... 24649 A/78

[51] Int. Cl.$^3$ ........................ C07C 31/20; C07C 29/17
[52] U.S. Cl. .................................................. 568/861
[58] Field of Search ......................................... 568/861

[56] References Cited

U.S. PATENT DOCUMENTS

| 3,055,840 | 9/1962 | Koch | 568/881 |
| 3,847,989 | 11/1974 | Platz et al. | 568/861 |
| 3,950,441 | 4/1976 | Rudoff et al. | 568/861 |
| 4,011,277 | 3/1977 | Nishida et al. | 568/861 |

OTHER PUBLICATIONS

Rylander et al., "Chem. Abstracts", vol. 55(1961), 24516g.

Primary Examiner—J. E. Evans
Attorney, Agent, or Firm—Sughrue, Mion, Zinn, Macpeak and Seas

[57] ABSTRACT

A process for producing 1-4 butanediol comprising reacting 1-4 butynediol with hydrogen in the presence of a catalyst comprising ruthenium and palladium in a weight ratio of about 4:1, at a temperature of from 60° to 180° C. and at a pressure of between 1 to 50 bars.

7 Claims, No Drawings

PROCESS FOR THE CATALYTIC HYDROGENATION OF 1-4-BUTYNEDIOL TO 1-4 BUTANEDIOL

This is a continuation of application Ser. No. 184,838, filed Sept. 8, 1980, now abandoned, which is a divisional application of Ser. No. 49,245, filed June 18, 1979, now abandoned.

BACKGROUND TO THE INVENTION

The invention relates to a catalyst for catalytic hydrogenation of 1-4 butynediol to 1-4 butanediol.

As is known, the aforementioned hydrogenation reaction of 1-4 butynediol (1) to 1-4 butanediol (III) passes through an intermediate phase in which 1-4 butanediol (II) is produced in accordance with the following equation:

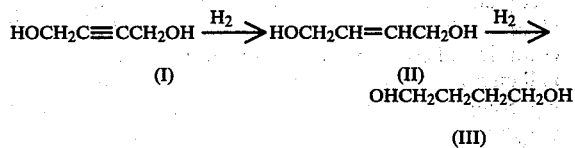

It is also known that the aforementioned hydrogenation reaction is accompanied by a secondary isomerization reaction of 1-4 butenediol (II) to form a by-product comprising γ-hydroxy-butyraldehyde: $HOCH_2CH_2CH_2CHO$ (IV).

This secondary reaction depends on the nature of the catalyst used and on the conditions (temperature and pressure) chosen for hydrogenation of 1-4 butynediol. As is well known, the side-reaction is favoured by the presence of hydrogen, particularly when noble metals are used as catalysts. Consequently, at the end of the catalytic hydrogenation of 1-4 butynediol, the reaction mixture inevitably contains a varying but always substantial amount of γ-hydroxybutyraldehyde. As is known, this results in serious problems when practically quantitative yields are required in the aforementioned reaction, e.g. when applied on an industrial scale.

In order to avoid the presence of γ-hydroxybutyraldehyde in the final product, and in view of the impossibility of preventing the side-reaction of isomerization of 1-4 butenediol, it is necessary to ensure that the aldehyde group of γ-hydroxybutyraldehyde is effectively hydrogenated to a corresponding alcohol group, at the same rate as it is formed.

However, it is known that hydrogenation of an aldehyde group is less easy than saturation of a double or triple bond. Furthermore, catalysts suitable for hydrogenation of unsaturated bonds generally have little or no activity in the hydrogenation of carbonyl groups.

Consequently, in order to obtain acceptable industrial yields the most common prior-art method of catalytic hydrogenation of 1-4 butynediol makes use of a catalyst based on nickel and copper in a ratio of about 4:1.

Owing to the known low activity of the last-mentioned catalyst, the hydrogenation of 1-4 butynediol is brought about at very high pressures, of the order of 200-300 bars, and at temperatures of the order of 140° C. or more, with all the adverse consequences which are well known to the skilled addressee.

In addition the reaction is very slow, which seriously affects the overheads of the aforementioned method of hydrogenation when on an industrial scale.

U.S. Pat. Nos. 2,953,605, 2,967,893, 2,950,326 and 3,449,445 teach the use of Raney type catalyst, based as before on nickel and copper, in one or more stages. This does not substantially reduce the aforementioned technical disadvantages and also, as is known, results in technical complications resulting from a "Ranning catalyst" method and the dangers of using pyrophoric catalysts.

With reference to the use of noble metals as catalysts in a hydrogenation reaction of unsaturated bonds, the basic, unvarying teaching of the hitherto available technical literature is to make predominant use of palladium. However, in view of the high isomerizing power of this metal particularly in the presence of hydrogen, and its known low capacity to hydrogenate aliphatic aldehyde groups to corresponding alcohol groups, it has been suggested that catalytic hydrogenation of 1-4 butynediol should be brought about by using palladium mixed if required with a predetermined percentage of zinc, but only to bring about conversion to 1-4 butenediol, using extremely mild hydrogenation conditions to prevent isomerization of the 1-4 butenediol to γ-hydroxybutyraldehyde, or using catalysts based as before on palladium but suitably poisoned.

The hitherto available technical literature also teaches that ruthenium in one of the most most efficient metals for catalyzing the hydrogenation of aldehyde groups to corresponding alochol groups, but its capacity to catalyze the reduction of unsaturated bonds is so low that it is nowhere recommended for this purpose.

If it is desired to bring about catalytic hydrogenation by using a two-metal catalyst system, one metal favouring the saturation of unsaturated bonds and the other metal favouring the hydrogenation of the aldehyde group (e.g. using nichel and copper or palladium and zinc), the consistently deducible and hitherto confirmed teaching in the technical literature is that the percentage of metal used for hydrogenating the aldehyde group should be appreciably lower than the percentage of the metal chosen as the catalyst for reducing the unsaturated bonds. It is known, however, that hydrogenation based on the aforementioned teaching has not been conveniently or widely applied on an industrial scale, mainly because of the pressure and temperature conditions required for completing the hydrogenation reaction, the low yields and the low reaction rates, which increase the expense of industrial production of the desired saturated compound.

At present 1-4 butanediol is being increasingly used in expanded polyurethane, in polyurethane polymers, in saturated polyesters and in fine chemicals. Its use for these purposes could be greatly increased, both quantitatively and qualitatively, if it could be more cheaply produced.

SUMMARY OF THE INVENTION

Accordingly the invention is based on the problem of providing a catalyst for catalytic industrial hydrogenation of 1-4 butynediol to 1-4 butanediol which completely obviates the aforementioned disadvantages of the prior art.

To this end, according to the invention, the catalyst comprises ruthenium and palladium.

Advantageously, according to a second feature of the invention, the weight ratio of ruthenium to palladium in the catalyst is at least 1:1.

More particularly, in a preferred embodiment, the invention provides a catalyst for catalytic hydrogenation of 1-4 butynediol to 1-4 butanediol, the catalyst comprising ruthenium and palladium and the weight ratio of ruthenium to palladium being 4:1.

The main advantages of the invention are that, when the catalyst is based on ruthenium and palladium in the aforementioned proportions, the catalytic hydrogenation reaction, on an industrial scale, of 1-4 butynediol to 1-4 butanediol is completed with quantitative yields under pressure and temperature conditions which are critically more advantageous economically than those hitherto necessary when using the prior-art catalysts. It has been found, as will be shown in the examples hereinafter, that the catalytic hydrogenation reaction using the catalysts according to the invention can be completed with quantitative yields and at pressures varying from 1 to 50 bars and at temperatures from 60° to 180° C.

It is important to stress that these results, which are extremely advantageous and not only in the eyes of the skilled addressee, are obtained by using a catalyst containing two metals (ruthenium and palladium) in which the ratio of the metal (ruthenium) used to reduce aliphatic aldehyde groups to the metal (palladium) used to hydrogenate unsaturated bonds is completely different from the ratios conventionally taught in the appropriate branch of the technical literature and hitherto generally used, e.g. the ratios of nickel to copper and palladium to zinc. There is thus a marked contrast from the prior art.

DETAILED DESCRIPTION

Other features and advantages will be clear from the following examples, given by way of illustration only, of a method of producing 1-4 butanediol by catalytic hydrogenation of 1-4 butynediol, using a catalyst according to the invention. Some comparative examples are also given, in which the same catalytic hydrogenation method is followed by prior art catalysts are used for comparison.

In all these examples, use was made of a tilting hydrogenation autoclave having a capacity of about 4 liters (1 U.S. gallon) equipped with a thermometer tube, an inlet and an outlet duct for gas, and a discharge duct at the bottom for total recovery of the reaction product. In all the examples, the method of operation and the parameters were standardized as follows:

Pressure: 30 bars,
Temperature: 110° C.,
Percentage total weight of catalyst used: 5%,
Reaction time: 2 hours.

For simplicity, and in order more clearly to show the results, the examples are grouped in the following Table, in which comparative examples are indicated by capital letters whereas examples according to the invention are indicated by serial numbers.

The catalytic hydrogenation of 1-4 butynediol was brought about either without a solvent (comparative Example D and Example 6 according to the invention) or in the presence of water (comparative Example C and Example 5 according to the invention) or organic solvents. The organic solvents used were polar solvents which cannot become hydrogenated under the test conditions. The standard solvent used in the comparative examples A, B and Examples 1, 2, 3 and 4 according to the invention was ethylene glycol dimethyl ether, commercially known as Dowanol MG (DMG).

An examination of the Table shows immediately that a solvent, either aqueous or organic, can be used to obtain higher yields in a given reaction time. Under all conditions, however, the combination of ruthenium and palladium in the catalyst is the decisive factor in ensuring complete conversion of 1-4 butynediol to 1-4 butanediol.

TABLE

| Example | BIN (grams) | Solvent | Catalyst | Grams of catalyst | Temp. °C. | BIN's Conversion | SELECTIVITY to BAN[1] | BEN[2] |
|---|---|---|---|---|---|---|---|---|
| A | 430 | DMG 450 | Ru/C (5% Ru) | 5 g | 110 | 57 | 64 | 33 |
| B | 430 | DMG 450 | Pd/C (5% Pd) | 5 g | 110 | 80 | 71 | — |
| 1 | 430 | DMG 450 | Pd/C—Ru/C (1:1) | 5 g | 110 | 89 | 75 | 21 |
| 2 | 430 | DMG 450 | Pd/C—Ru/C (1:2) | 5 g | 110 | 75 | 89 | 10 |
| 3 | 430 | DMG 450 | Pd/C—Ru/C (1:4) | 5 g | 110 | 100 | 100 | — |
| 4 | 430 | DMG 450 | Pd/C—Ru/C (4:1) | 5 g | 110 | 85 | 74 | 7 |
| C | 430 | $H_2O$ 450 | Ni Raney | 5 g | 110 | 65 | 58 | 41 |
| 5 | 430 | $H_2O$ 450 | Pd/C—Ru/C (1:4) | 5 g | 110 | 100 | 97 | 3 |
| D | 700 | — | Pd/C | 5 g | 110 | 80 | 69 | — |
| 6 | 700 | — | Pd/C—Ru/C (1:4) | 5 g | 110 | 100 | 90 | 8 |
| 7 | 430 | DMG 450 | Pd/$Al_2O_3$—Ru/$Al_2O_3$ (1:4) | 5 g | 110 | 100 | 95 | 4 |

TABLE
Pd/C = palladium on carbon
Ru/C = ruthenium on carbon
Pd/$Al_2O_3$ = palladium on alumina
Ru/$Al_2O_3$ = ruthenium on alumina
BAN[1] = 1-4 butanediol
BEN[2] = 1-4 butenediol
BIN = 1-4 butynediol It is also clear that the weight ratio of ruthenium to palladium is an essential factor in the selectivity of the catalytic hydrogenation reaction, since the ratio increases together with the selectivity to 1-4 butanediol, reaching a value of 100 (quantitative yield) when the ruthenium/palladium ratio is 4:1.

Excellent results are also obtained when the catalyst, comprising ruthenium and palladium combined in the ratio 4:1, is on an alumina carrier. Additional catalytic hydrogenation tests using ruthenium and palladium on alumina showed that the conversion yields and selectivity with regard to 1-4 butanediol were practically 100% when the reaction time ws 2½ hours.

Other tests showed that the pressure can be (appreciably) reduced to values of the order of 1-5 bars with yields still equal to those given in the table, except that the reaction times were considerably longer. The reaction temperature can also be widely varied. It has been found that it is not usually convenient to bring about catalytic hydrogenation, using the catalytic according to the invention, at temperatures below 60°-70° C. without excessively prolonging the reaction times, whereas the temperature should be below 180° C. to avoid initiating a monodehydration reaction in which the 1-4 butanediol product is converted to tetrahydrofuran.

The process of producing 1-4 butanediol using a catalyst according to the invention as shown in the examples, has been easy to apply on an industrial scale. The results have been as shown and the production of 1-4 butanediol has been considerably more economic than that hitherto possible, using processes based on prior-art catalysts.

The ruthenium/palladium catalyst according to the invention can be prepared in any conventional manner, e.g. by mixing the various metals on separate carriers in predetermined proportions, or by simultaneously absorbing them on an appropriate carrier.

What is claimed is:

1. A process for producing 1-4 butanediol comprising reacting 1-4 butynediol with hydrogen in the presence of a catalyst comprising ruthenium and palladium in a weight ratio of about 4:1, at a temperature of from 60° to 180° C. and at a pressure of between 1 to 50 bars.

2. The process of claim 1, wherein said reacting is carried out in the presence of a solvent.

3. The process of claim 1, wherein said reacting is carried out for about 2.5 hours.

4. The process of claim 1, wherein said catalyst is supported on an alumina carrier.

5. The process of claim 1, wherein the temperature is 110° C. and the pressure is 30 bars.

6. A process for producing 1-4 butanediol comprising reacting 1-4 butynediol with hydrogen in the presence of a catalyst comprising ruthenium and palladium in a weight ratio of about 4:1, in a solvent at a temperature of about 110° C. and at a pressure of about 30 bars for a period of about 2 hours.

7. The process of claim 6, wherein the solvent is ethylene glycol dimethyl ether.

* * * * *